(12) United States Patent
Luinge et al.

(10) Patent No.: US 7,725,279 B2
(45) Date of Patent: May 25, 2010

(54) SYSTEM AND A METHOD FOR MOTION TRACKING USING A CALIBRATION UNIT

(75) Inventors: Hendrik Johannes Luinge, Enschede (NL); Daniel Roetenberg, Enschede (NL); Per Johan Slycke, Deventer (NL)

(73) Assignee: Xsens Technologies, B.V. (NL)

( * ) Notice: Subject to any disclaimer, the term of this patent is extended or adjusted under 35 U.S.C. 154(b) by 0 days.

(21) Appl. No.: 12/049,019

(22) Filed: Mar. 14, 2008

(65) Prior Publication Data

US 2008/0262772 A1  Oct. 23, 2008

(30) Foreign Application Priority Data

Mar. 15, 2007 (EP) ................... 07104283

(51) Int. Cl.
*G01C 25/00* (2006.01)
(52) U.S. Cl. .................... 702/94; 702/150; 702/152; 702/153
(58) Field of Classification Search ............. 702/94–95, 702/190, 141, 150, 153; 73/488
See application file for complete search history.

(56) References Cited

U.S. PATENT DOCUMENTS

| | | | |
|---|---|---|---|
| 4,106,094 A | 8/1978 | Land | |
| 5,645,077 A | 7/1997 | Foxlin | |
| 5,744,953 A | 4/1998 | Hansen | |
| 6,361,507 B1 | 3/2002 | Foxlin | |
| 6,474,159 B1 | 11/2002 | Foxlin et al. | |
| 6,691,074 B1 | 2/2004 | Moriya et al. | |
| 6,820,025 B2 | 11/2004 | Bachmann et al. | |

FOREIGN PATENT DOCUMENTS

EP        07104283       3/2007

| NL | 1030440 | 5/2007 |
|---|---|---|
| WO | WO 2007/058526 A1 | 5/2007 |

OTHER PUBLICATIONS

U.S. Appl. No. 11/748,963, filed May 15, 2007, Luinge et al.

(Continued)

*Primary Examiner*—Drew A Dunn
*Assistant Examiner*—Hien X Vo
(74) *Attorney, Agent, or Firm*—Leydig, Voit & Mayer, Ltd.

(57) ABSTRACT

The invention relates to motion tracking system (10) for tracking a movement of an object (P) in a three-dimensional space, the said object being composed of object portions having individual dimensions and mutual proportions and being sequentially interconnected by joints the system comprising orientation measurement units (S1, S3, . . . SN) for measuring data related to at least orientation of the object portions, wherein the orientation measurement units are arranged in positional and orientational relationships with respective object portions and having at least orientational parameters; a processor (3, 5) for receiving data from the orientation measurement units, the said processor comprising a module for deriving orientation and/or position information of the object portions using the received data and a calibration unit (7) arranged to calculate calibration values based on received data and pre-determined constraints for determining at least the mutual proportions of the object portions and orientational parameters of the orientation measurement units based on received data, pre-determined constrains and additional input data. The invention further relates to a method for tracking a movement of an object, a medical rehabilitation system and an animation system.

29 Claims, 6 Drawing Sheets

OTHER PUBLICATIONS

U.S. Appl. No. 12/093,914, filed May 15, 2008, Slycke et al.
Product Brochure entitled "Moven by Xsens, Innovator in Inertial Sensor Technology", Copyright 2007, pp. 1-3.
International Search Report for PCT/NL2006/000572 filed Nov. 15, 2006, pp. 1-10.
Roetenberg, D., "Inertial and Magnetic Sensing of Human Motion", Ph.D. thesis, Universtity of Twente, obtained from the Internet on Jun. 9, 2008 at http://www.xsens.com/Static/Documents/UserUpload/papers/Inertial%20and%20Magnetic%20Sensing%20of%20Human%20Motion.pdf, Copyright 2006, pp. 1-127.
Luinge, H.J., "Inertial Sensing of Human Movement", Ph.D. thesis, University of Twente, obtained from the Internet on Jun. 9, 2008 at http://www.xsens.com/Static/Documents/UserUpload/papers/Inertial_Sensing_of_Human_Movement_Thesis_Luinge.pdf, , Copyright 2002, pp. 1-80.

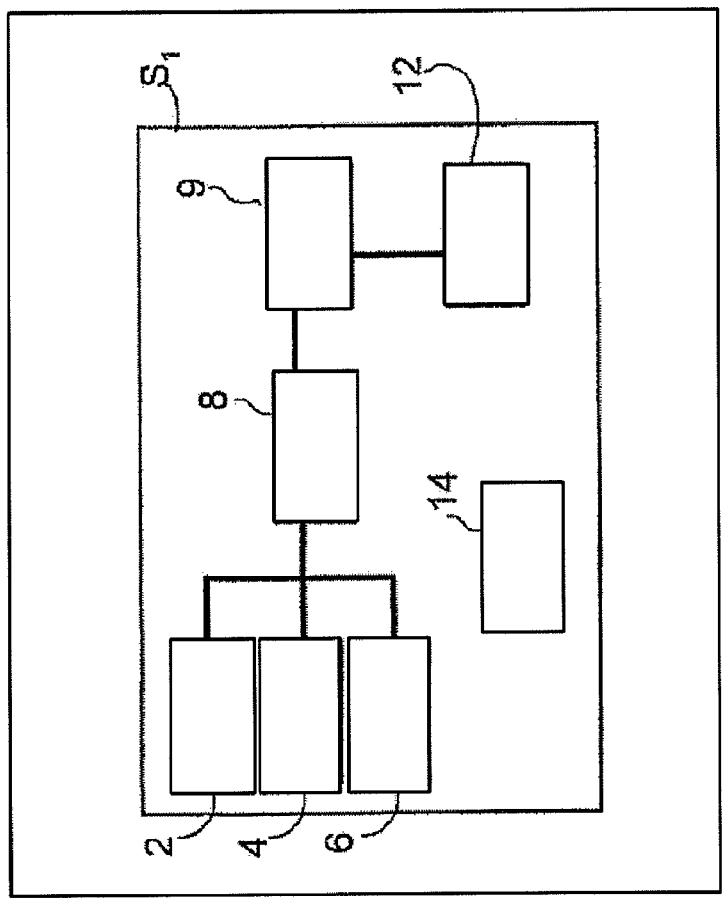
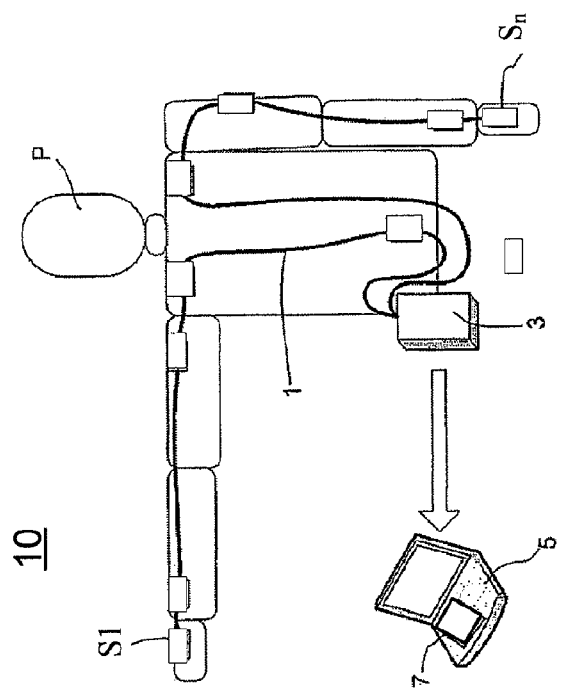
Fig. 1

SYSTEM AND A METHOD FOR MOTION TRACKING USING A CALIBRATION UNIT

CROSS REFERENCE TO RELATED APPLICATIONS

This patent application claims priority to European Patent Application No. 07104283.2 filed Mar. 15, 2007, which is herein incorporated by reference in its entirety for all that it teaches without exclusion of any part thereof.

FIELD OF THE INVENTION

The invention relates to a motion tracking system for tracking a movement of an object in a three-dimensional space, the said object being composed of object portions having individual dimensions and mutual proportions and being sequentially interconnected by joints, the system comprising:

orientation measurement units for measuring data related to at least an orientation of the object portions, wherein the orientation measurement units are arranged in positional and orientational relationships with respective object portions having at least orientational parameters;

a processor for receiving data from the orientation measurement units, the said processor comprising a module for deriving orientation and/or position information of the object portions using the received data.

The invention further relates to a method for tracking a movement of an object being composed of object portions having individual dimensions and mutual proportions and being interconnected by joints in a three-dimensional space.

BACKGROUND OF THE INVENTION

Many different disciplines use motion analysis systems to capture movements and postures of the human body. To make realistic animations for movies and computer games, movements of the actor are captured and mapped onto a character. In sports, motion analysis techniques are used to analyze and improve performances. In the field of medicine and rehabilitation, recordings of human motion can be used, for example, to evaluate gait patterns.

Three dimensional (3D) motion capturing is generally performed using magnetic or camera-based systems. In camera-based systems, reflective or light-emitting markers attached to the body are observed by a number of cameras from which the 3D position can be reconstructed using triangulation of each camera 2D image. With magnetic trackers, magnetic field sensors measure the field as emitted by a source placed near the subject from which position and orientation of the magnetic field sensor with respect to the source can be calculated. The set-up of external emitters or cameras limits the working area where the subject can be captured and impedes many applications.

To capture the three dimensional human body movements and postures without the need for external emitters or camera's, miniature Orientation measurement units (OMU) can be placed on several body segments. These OMU can be arranged to measure their own motion with respect to an earth-fixed reference system or they can be arranged to measure relative orientation.

Orientation measurement units (OMU), notably inertial sensors, magnetic coils, goniometers, mechanical orientation sensing devices, or the like, can be used to record the movement of a subject i.e. an actor or a patient. The subject is described as an articulated body. By knowing the orientation of the segments as well as the relative distance between the joints, the complete body pose can be derived. An important requirement is that the pose orientation of the OMU with respect to the body segments must be known as well as the relative distances between joints.

In the known orientation measurement systems use is made of sequentially interconnected body portions connected by joints. To enable motion tracking, respective relative dimensions of the body portions constituting the said sequence must be known. The values of the dimensions are used for the distance between respective joints. Also, at least an orientation of the OMU with respect to the body portion must be known.

In order to enable motion tracking, the known motion tracking systems must be subjected to a step of calibration wherein both the orientation of the OMU's with respect to the body portions and at least a relative distance between the joints are determined. In an embodiment of the known motion tracking system such calibration step is performed by measuring the dimensions of the body portions and by collecting data from the OMU's when a person is standing in a standard, pre-known pose, like a T-pose. Different techniques exist for obtaining necessary data for calibration, notably the orientation of the OMU with respect to the body portion, of such known system:

a) Carefully securing the OMU in a known pose to the body portion of interest. Palpation of for example bony landmarks may be required to determine this pose;

b) Asking the subject whose movement is to be measured to stand in a known pose, for example upright with arms downwards, or a so-called T-pose.

c) Asking the subject to perform a certain movement that is assumed to correspond to a certain axis. For example, the arm axis is defined by a pronation or supination movement. Measured orientation, or other quantity such as angular velocity, is used to find the orientation of the OMU with respect to the body portion. Such a technique is for example described in Luinge et al J. Biomech. 2007; 40(1): 78-85. Epub 2006 Feb. 7.

Different techniques exist for obtaining necessary data for calibration, notably the relative distances between joints of the body portions, of such known system:

The distance between the joints can be obtained using regression equations to obtain body dimensions. One or a few body dimensions are measured using e.g. a measuring tape, or by using position measurements derived from a camera system. The measured dimensions can be used as input to known standard tables to estimate the joint positions.

It is a disadvantage of the known system and method for obtaining the orientation of the OMU with respect to the body portions as well as the relative distances between joints in that substantial inaccuracies occur due to errors in palpation or errors in acquiring and sustaining a static pose. Further, the known methods lacks subject specificity because only a few measures are taken and the joint position can not be measured directly, but must be derived using regression equations based on average human dimensions.

An inertial measurement unit (IMU) comprises gyroscopes, which measure angular velocities, accelerometers which measure accelerations including gravity and optionally magnetometers measuring the earth magnetic field. Using these signals, the orientation with respect to gravity and the Earth magnetic field and acceleration of the IMU housing can be obtained. An embodiment of a method an apparatus for motion tracking using IMU is known from U.S. Pat. No. 6,820,025.

The known methods for obtaining necessary data for calibration when using an IMU as OMU are particularly disadvantageous because as an additional requirement the subject has to stand in a known pose with respect to gravity as well as with respect to a local magnetic field. This latter condition places an extra burden on the subject.

SUMMARY OF THE INVENTION

It is an object of the invention to provide a system and a method for motion tracking wherein the calibration step, providing data on at least orientation of the OMU on a body portion and relative proportions between the body portions constituting a sequence interconnected by joints, is performed with increased accuracy.

To this end in the system according to the invention the processor comprises a calibration unit arranged to calculate calibration values for determining at least mutual proportions of the object portions and at least orientational parameters of the orientation measurement units based on received data, pre-determined constraints and additional input data comprising knowledge about a distance between at least two points and/or knowledge about an acceleration of at least two object portions connected by a joint.

Preferably, the pre-determined constraints comprise geometrical and/or mechanical constraints pertaining to the sequential interconnection of the object portions. The technical measure of the invention is based on the insight that by combining measurements from the orientation measurement units with certain knowledge, the calibration procedure can be kept simple yet calibration values can be determined with increased accuracy, leading to an increase of motion tracking accuracy. In case when the input data comprises orientation of the OMU and the said knowledge, the calibration results in determining or correcting data on OMU's orientation with respect to a body portion as well as determining or correcting data with respect to the mutual proportions of the body portions. As an additional advantage, the motion tracking system according to the invention does not require any assistance of a further person for enabling the calibration step.

It is noted that the orientation measurement units may comprise inertial sensors comprising gyroscopes and accelerometers. Sometimes, such inertial sensors may comprise a magnetometer arranged in the same housing. Using such inertial sensors measurement data pertaining to both an orientation and an acceleration of a body portion can be determined. It is further noted that in accordance to the invention two different calibration methods carried out by the calibration unit are envisaged:

method I: determining orientation of the OMU with respect to a body portion and determining relative proportions between object portions. For implementation of this method it is required that the OMU is arranged for determining orientation data pertaining to the OMU itself.

method II: determining position and orientation of the OMU and determining relative proportions between the object portions. For implementation of this method it is required that the OMU is arranged for determining orientation and acceleration data pertaining to the OMU itself.

It is further noted that the term pre-determined constraints, used in the present context relates to the following knowledge and/or mathematical equations suitably describing such knowledge:

the fact that the body portions form a kinematic chain interconnected by joints, whereby each joint substantially coincides with an area of the respective anatomical joint. Hereby kinematic constraints are formed based on knowledge about allowable movements of body portions connected by joints, thereby constituting a kinematic chain. Kinematic constraints, also referred to as joint constraints are further discussed with reference to FIG. 3.

mechanical boundary conditions pertaining to a redundancy in certain motion patterns; such as known shoulder movement synergies or neurological synergies as also mentioned in the last paragraph.

geometric and mechanical constraints pertaining to a unit structure. The unit structure is defined as two body portions interconnected by a joint. This is further described with reference to FIG. 3;

antropometric parameters of a model person used for calibration, said antropometric parameters pertaining to either of the following: measurements of at least one dimension of at least one body portion of the model person; scaling data pertaining to ratio's between different body portions constituting the model person, a priori knowledge about population specific parameters, a priori knowledge about location of sensor on the body.

Additional input data suitable for use in method I:

Knowledge about a distance. For example, instead of measuring respective body portion of the model person, it is sufficient to consider that a distance between two points is kept the same, or kept zero, while measurement data are being collected during a specific elementary movement or pose. This is further described with reference to FIG. 4. Additionally or alternatively, it is sufficient to consider that a dimension in a specific direction is known. This embodiment of the pre-determined constraint pertains to a situation when the model person is standing on a flat surface whereby it is known that a vertical difference between a left-hand side and the right-hand side of the body is zero.

Additional input data suitable for use in method II:

The acceleration, measured at two different object portions, connected by a joint. In accordance with another embodiment of the motion tracking system according to the invention, the measurement data pertaining to acceleration of the OMU with respect to two points on the respective body portions is used together with suitably selected pre-determined constraints, notably the joint constraints or a knowledge about a distance between two points, for determining two parameters of the OMU, notably the orientation and the position of the OMU with respect to the joints. In addition also absolute individual dimensions of the body portions are determined.

The measurement data required from the OMUs can be obtained from a recording in which:

method I. It is known that one point A defined on a body portion is kept at a known or constant distance with respect to a point B defined on a body portion. This could be conducted by instructing a person to keep one part of the body in contact with another part. This method will find the relative distance between joints as well as the orientation of the OMUs with respect to the body portion. This technique is further described with reference to FIG. 4 and FIG. 5.

method II. The OMUs are equipped to also measure acceleration. The subject makes arbitrary movement where the body portions undergo acceleration. This technique is further described with reference to FIG. 6.

It is mentioned that in a first embodiment discussed above a relative dimension and a direction of vectors between two joints in a chain is determined with respect to an OMU, whereas in the second embodiment discussed above also a position of the OMU with respect to the joint is determined.

In a further embodiment of the motion tracking system according to the invention the pre-determined constraints are statistically expressed. Notably, all values may be assigned with a confidence interval. For example, a joint may have a certain laxity, which may be statistically described as an uncertainty in a suitable value.

In case when the measurement data further relate to the position and/or orientation of the orientation measurement unit, the calibration unit may be further advantageously arranged to statistically express the parameters of the orientation measurement units.

It is found to be advantageous to introduce a measure of uncertainty to the above-described constraints and/or measurement data. In particularly, this applies to scaling and further antropometric parameters. It is further noted that in case when the pre-determined constraints are statistically expressed, the calibration unit can be arranged to find a best solution for the calibration values in statistical sense. This is advantageous because in this case a suitable computation routing converges faster to results. Next, apart from a best estimate of the calibration values, also a statistical error bound to the resulting calibration values can be obtained for each parameter. This has the advantage that in case there is a reason that some parts of the calibration procedure are less accurate, these inaccuracies can be taken into account. For example, in case of an environment with large earth magnetic disturbance, a reliance on magnetometers can be automatically reduced. The same applies when measurements are less reliable because a person being tracked may experience having difficulties performing certain movements, in particular rehabilitating patients. Preferably, the calibration unit is further arranged to assign a weighting factor to an individual parameter in relation with the calculated statistical error. Preferably, expected accuracy or consistency is fed back to the user.

It is a further embodiment of the motion tracking system according to the invention further comprises a control unit arranged to control the processor for discarding measurement data from an orientation measurement unit which provides data used for calculation of a parameter with a reduced weighting factor.

This particular embodiment is advantageous because data from an OMU providing less reliable readings can easily be eliminated from an algorithm for obtaining calibration values for use in calculation of individual parameters of the body portions and parameters of the OMU. Preferably, the calibration unit is arranged to use a pre-defined model of the object for determining individual parameters of the object portions and/or parameters of the orientation measurement units. A suitable example of a kinematic model is described with reference to FIG. 3. It is also possible that the individual parameters of the body portions are a-priori correlated. It is also possible that for certain pre-defined model scaling equations are introduced which describe correlations between different measurements of respective body portions in statistical terms to use an estimate of parameters of the orientation measurement units.

Preferably, in the system according to the invention the individual dimensions and/or mutual proportions of the object portions are a-priori correlated.

In a further embodiment of the motion tracking system according to the invention the calibration unit is further arranged to use an initial estimate of the calibration values. In this way the calibration values are being adjusted based on initial estimates. The system thereby operates iteratively.

Preferably, the calibration values are determined in a coordinate system definable by joints, see FIG. 3. This is contrary to the use of palpation where only bony landmarks can be palpated, because the relation between the bony landmarks and the functional joint location is not straightforward and can be subject to great individual variation in morphology.

Given a sufficient number of measurements, not only the body dimensions and the position and orientation of the sensor with respect to the segment can be obtained, but also the captured movement itself can be refined. Preferably, in the motion tracking system according to the invention the orientation measuring device comprises an inertial sensing unit.

The method according to the invention comprises the steps of:

measuring data related to at least an orientation of the object portions with orientation measurement units, wherein the orientation measurement units are arranged in positional and orientational relationships with respective object portions having at least orientational parameters;

receiving data from the orientation measurement units;

deriving orientation and/or position information of the object portions using the received data;

calculating calibration values for determining at least mutual proportions of the object portions and at least orientational parameters of the orientation measurement units based on received data, pre-determined constraints and additional input data comprising knowledge about a distance between at least two points and/or knowledge about an acceleration of at least two object portions connected by a joint.

The method of the invention is further described with reference to FIG. 2. The procedure corresponding to the method according to the invention is extremely flexible. If some parts of the procedure are difficult to perform, they can be omitted with a slight compromise in accuracy. Also, if one is only interested in a certain aspect of the movements, such as recording grasping movements, the calibration procedure can be limited and optimized for those movements. Further advantageous embodiments of the method according to the invention are set forth in Claims 16-28. It is noted that the system and the method as is set forth above are suitable for performing motion tracking of humans or animals. Also, it is noted that applicability of the system and the method according to the invention is not restricted to a confined space. Animals which movements could be captured using the system and the method according to the invention are, but not limited to horses, birds, elephants or dogs.

Contrary to the use of regression equations that contain standard dimensioning relations, the method is very subject specific. However, if desired the use of regression equations can still be seamlessly integrated in the procedure. This can be an advantage to even further speed up the calibration procedure.

Because the method finds the best estimate in a statistical sense, the different measurements can be seamlessly combined. Apart from a best estimate, also a statistical error bound can be obtained for each parameter to be estimated. Moreover, if there is reason that some parts of the procedure are less accurate, these inaccuracies can be taken into account. For example, in the case of an environment with large earth magnetic disturbance, the reliance on magnetometers can be automatically reduced. The same applies when measurements are less reliable because patients may have more difficulty to perform a certain movement. Because of its flexibility, the procedure can be combined with different techniques such as described above.

The invention further relates to a medical rehabilitation system. This system could be used to conduct research, diagnosis or therapy in the field of biomechanics, rehabilitation or ergonomics, wherein recording of motion of a patient and, preferably, follow-up on a possible progress in the motion patterns are enabled.

The invention further relates an animation system comprising the motion tracking system as is set forth in the foregoing.

This system could be used to record movement that can be used to drive animations in for example movies and computer games.

The invention further relates to a system as is set forth in the foregoing used in tracking the movement for the purpose of an input device to control computer games or computer simulations. In this way, real-time movement of a person can be used to control the game, or may be incorporated in the game, for example, by supplying a character in the game with movements of the gaming person. Those skilled in the art will appreciate that various modification of stipulated applications of the motion tracking system are possible without departing the technical measure of the invention.

BRIEF DESCRIPTION OF THE DRAWINGS

These and other aspects of the invention will be further discussed with reference to figures.

FIG. 1 presents in a schematic way an embodiment of a motion capture systems according to the invention;

DETAILED DESCRIPTION

Figure 2:
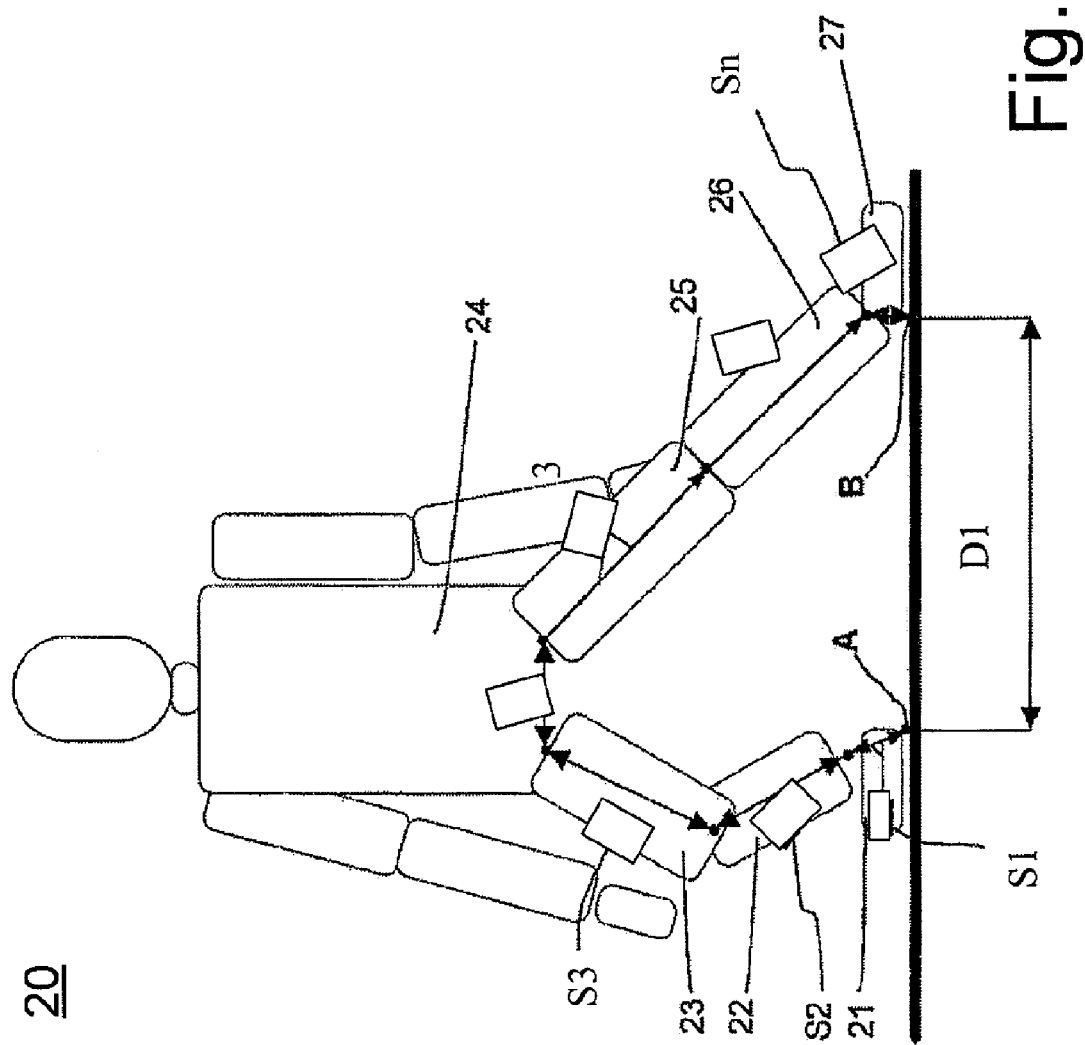
FIG. 2 presents in a schematic way an embodiment of a method according to the invention.

FIG. 1 presents in a schematic way an embodiment of a motion capture systems according to the invention. The system 10 comprises of a number of orientation measurement units S1, ..., Sn, notably inertial and magnetic sensor modules comprising suitable sensors, like 3D gyroscope 2, 3D accelerometer 4, 3D magnetic sensor 6. Notably, linear accelerometers possibly combined with magnetometers can be used for orientation measurement devices. Preferably, the orientation measurement units are arranged for each body segment to be tracked. The sensors may be connected to a bus system 3 which is arranged to provide the power supply for an sensors, synchronization of data sampling and, preferably, wireless transmission of all sensor and processed data to an external computer 7 or to any suitable logging device. The bus system 3 may contain one or more strings to which sensor modules are connected. Preferably, each sensor comprises a sensor sampling module 8, a digital signal processor 9. The strings and sensors are preferably embedded in a wearable, notably a suit which preferably fits tightly but comfortably to the skin of a person P. The suit is preferably designed to optimally mechanically fix the sensor to the body and to hide the cabling, if present. In an embodiment of the system 10 according to the invention, the sensor data are communicated to the processor 5 wirelessly. The wireless communication protocol can be Bluetooth, WiFi, UWB or alike. In an alternative embodiment of the system according to the invention each orientation measurement unit S1, ... Sn may be arranged to wirelessly communicate measurement data directly to the processor 5. Each sensor module can be expanded with a battery 14 and wireless communication module 12. This will eliminate the use of cables in the suit. The processor 5 is preferably arranged to handle synchronization between sensor modules. Alternatively, the sensors are arranged to enable mutual synchronization. All sensor data can be processed in the processor 5 using suitable per se known sensor fusion schemes. The processor 5 according to the invention comprises a calibration unit 7 arranged to determine individual parameters of the object portions and/or parameters of the orientation measurement units with respect to a coordinate system definable by joints based on received data and predetermined constraints. Preferably, suitable joint constraints and external contact constraints are applied on the received pre-processed data.

FIG. 2 presents in a schematic way an embodiment of a method according to the invention as is set forth in the Claim 17. In an embodiment of the method according to the invention use is made of the knowledge about a distance between two points A, B. It is noted that for implementation of the method it is sufficient that a distance between two points, for example hands, is kept constant during a movement. To this extent, a person may be asked to perform a series of movements keeping his hands separated at a certain distance. In order to ensure that this distance is not changed, the person may be asked to hold a suitable object, like a stick while displacing his hands. In an alternative embodiment, the person may be performing movements when standing on substantially flat surface. In this case it is known that a height difference between a left portion of the body and a right portion of the body is null. In accordance with the method of the invention the person 20 is modeled with a number of body portions 21 ... 27. Each body portion is characterized by the individual dimension, notably a (relative) length between its joints, and a 3D orientation of the OMU with respect to the body portion. A chain between the sequentially interconnected joints is identified starting at some point A and ending at some point B. The distance between the points A and B is known or constant. Preferably, each body portion in the chain is provided with a sensor S1, ..., Sn. Provided with the measurement data from the OMU's S1, ..., Sn and given knowledge about the distance D1, the following can be determined or refined:

a) the (relative) distance between the joints;

b) the (relative) distance between the first and last joint in the chain and point A and B, respectively;

c) the orientation of the OMU with respect to the line between the joints or points.

It is further noted that this calibration method is independent of the position of the OMU on a body portion.

Figure 3:
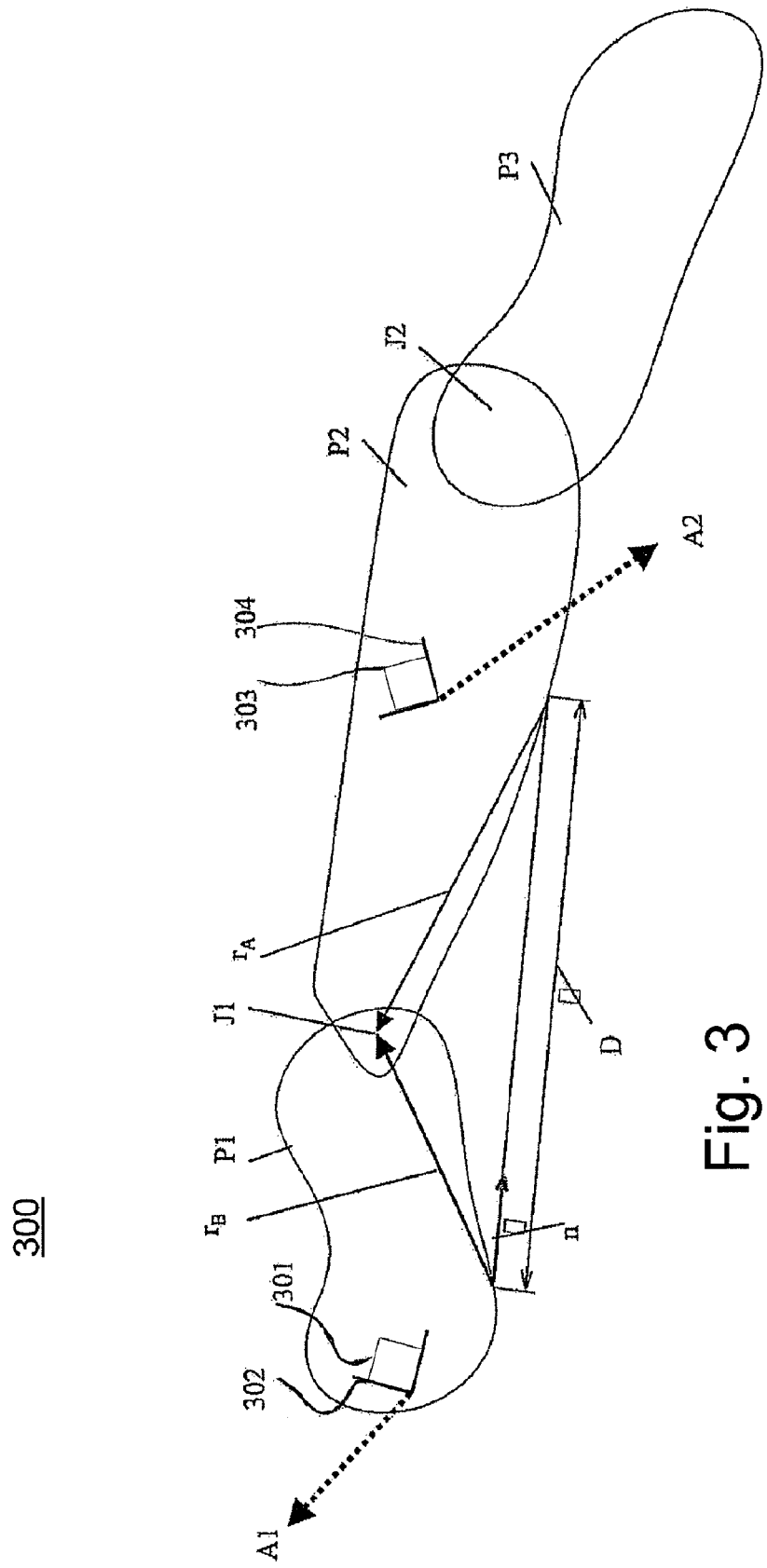
FIG. 3 presents in schematic way of an embodiment of three body portions interconnected by two joints in detail.

FIG. 3 presents a schematic way of an embodiment of three body portions interconnected by two joints in detail. FIG. 3 shows a kinematic chain of body portions P1, P2, P3, sequentially interconnected by joints J1, J2. The body portions P1 and P2 are provided with respective OMUs 301, 303, having respective coordinate systems 302, 304. The OMU's are positioned on respective body portions and are assigned with individual position and orientation parameters. The OMU's 301, 303 are arranged for measuring the orientation. Furthermore, some distance D is known or known to be constant, for example as is set forth with respect to FIG. 2. The following is derived:

A vector $^S r_i$ defined in a body portion i can be expressed in for example an earth fixed coordinate system G using amongst others the orientation of the OMU with respect to the body portion ($q_i$):

$$^G r_i = {}^G r_i(^S r_i, q_i)$$

Using a joint constraints the following equation holds in any coordinate system:

$$(r_A - r_B) \cdot n - D = 0$$

The large dot symbolizes the dot product, whereby n is the a-priori estimate of the unit vector giving the direction between two points. In the special case that the distance is zero, the equation may be written as $$r_A - r_B = 0$$

The quantities $^S r_A, ^S r_B, q_A, q_B$ are then refined in a statistical most-likely manner so that the constraint is met.

$$(^G r_A(^S r_A, q_A) - ^G r_A(^S r_B, q_B)) \cdot n - D = 0$$

A possible method to use this constraint to refine the parameters is as follows: The parameters to be estimated, $(^S r_A, q_A, ^S r_B, q_B)$ as well as possibly additional parameters to be estimated are a-priori correlated. If all parameters are contained in the column array x, the first order correlation can be written as $Q_x = E(x \cdot x^T)$, where the superscript T stands for transpose and the dot for vector/matrix multiplication. The above constraint can be linearized to $y = C \cdot x + v_t$, with y a column vector, C a matrix and v an unknown noise specifying the measurement inaccuracy with a correlation matrix R. Then the improved estimate is the well-known Kalman update:

$$x^+ = x + Q_x \cdot C^T (C \cdot Q_x \cdot C^T + R)^{-1} (y - C \cdot x)$$

Also an expression of the covariance of the improved estimate can be derived and is also given in most textbooks on Kalman filtering or statistical estimation.

It is noted that the all vectors do not necessarily need to be expressed in any specific coordinate system, like an earth-fixed coordinate system, but it is required that they are compared in the same coordinate system. It is further noted that the previous can be generalized using a chain of multiple segments as well as multiple causes of error in determining the vector $^G r$. The generalization principle is known per se for a person skilled in the art and will not be explained in detail. It is still further noted that if the distance is zero, three constraints can be generated because the distance is zero in three directions. In this particular embodiment use is made of pre-determined constraints related to joint constraints and the distance between two points D in respective body portions P1, P2.

If the OMU is configured to measure acceleration as well as orientation, for example if the OMU is an IMU, the position and orientation of the OMU with respect to the joint can be estimated, provided the acceleration is measured at least two points in a kinematic chain.

Given the orientation and acceleration A2 measured using an OMU on segment P2, the acceleration of the joint in an earth fixed reference frame can be estimated. This acceleration is a function of amongst others the OMU to joint vector $r_A$.

$$a_{jointA} = a_{jointA}(r_A)$$

If the same joint acceleration is also measured using the acceleration A1 on another segment P1, the following constraint can be made:

$$a_{jointA}(r_A) - a_{jointB}(r_B) = 0$$

Given a priori statistical properties of $r_A$ and $r_B$ as well as the uncertainty of the constraint, the vectors $r_A$ and $r_B$ can be refined according to the same equations described above. A person schooled in the building of statistical most likely estimators such as Kalman filters is able to make this statistical best estimate. It is hereby noted that the vectors $a_{jointA}$ and $a_{jointB}$ must be expressed in the same coordinate system. It is further noted that this method can be extended to a chain of multiple segments and it can also be generalized to more complicated models of joints and OMU movements.

Figure 4:
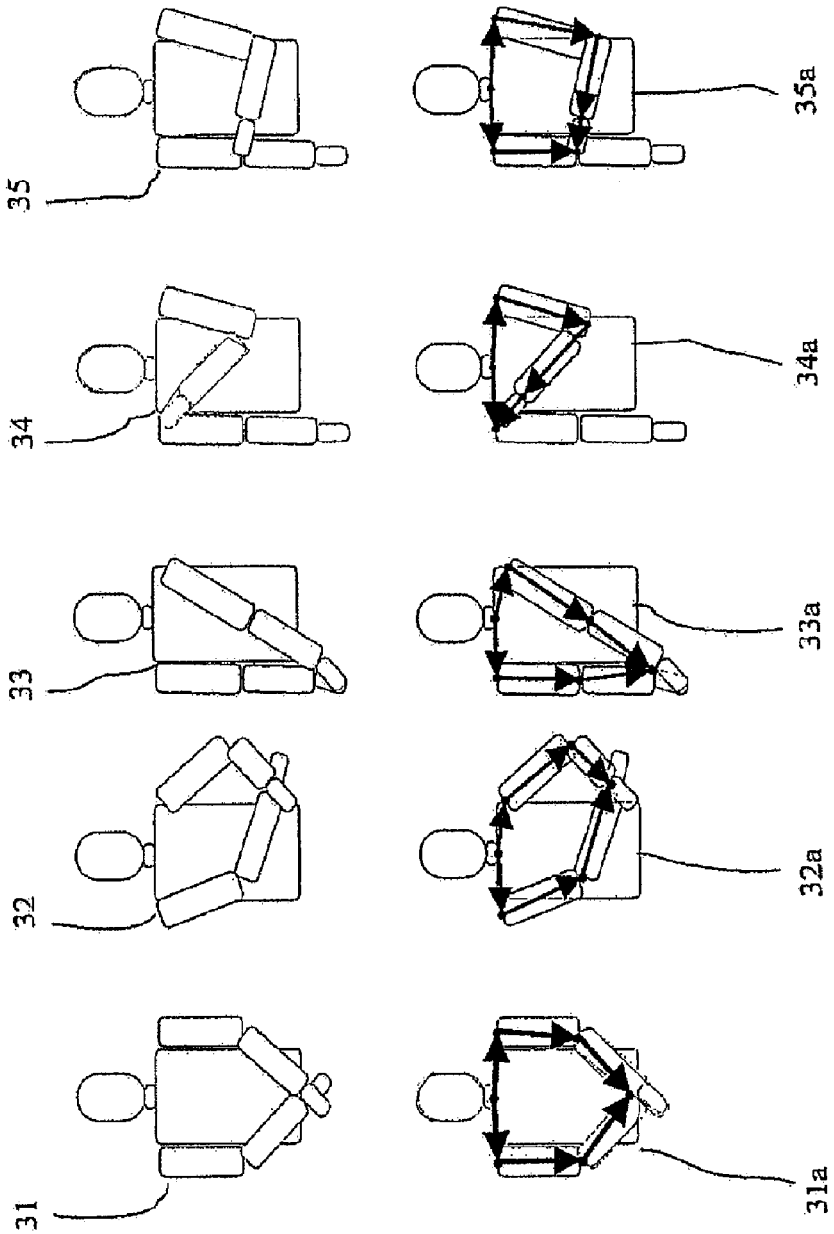
FIG. 4 presents in a schematic way an embodiment of a procedure for acquiring measurement data.

FIG. 4 presents in a schematic way an embodiment of a procedure for acquiring measurement data. A predefined sequence 30 of movements can be used to determine relative distance between joints as well as the orientation of the orientation measurement unit with respect to the segment. For example, for a pose 31, when the person makes a loop with his hands, a corresponding sensor-based loop is given by item 31a. It is noted that when measurement data pertaining to different loops is recorded, equations for scaling and positioning the object portions can be generalized thereby improving relative scaling of the object portions. By assembling the equations pertaining to the dimensions of the object portions and by merging them with the scale equations the calibration data are obtained. The calibration data is to be used to improve the tracking of a movement of the object in three dimensional space.

Figure 5:
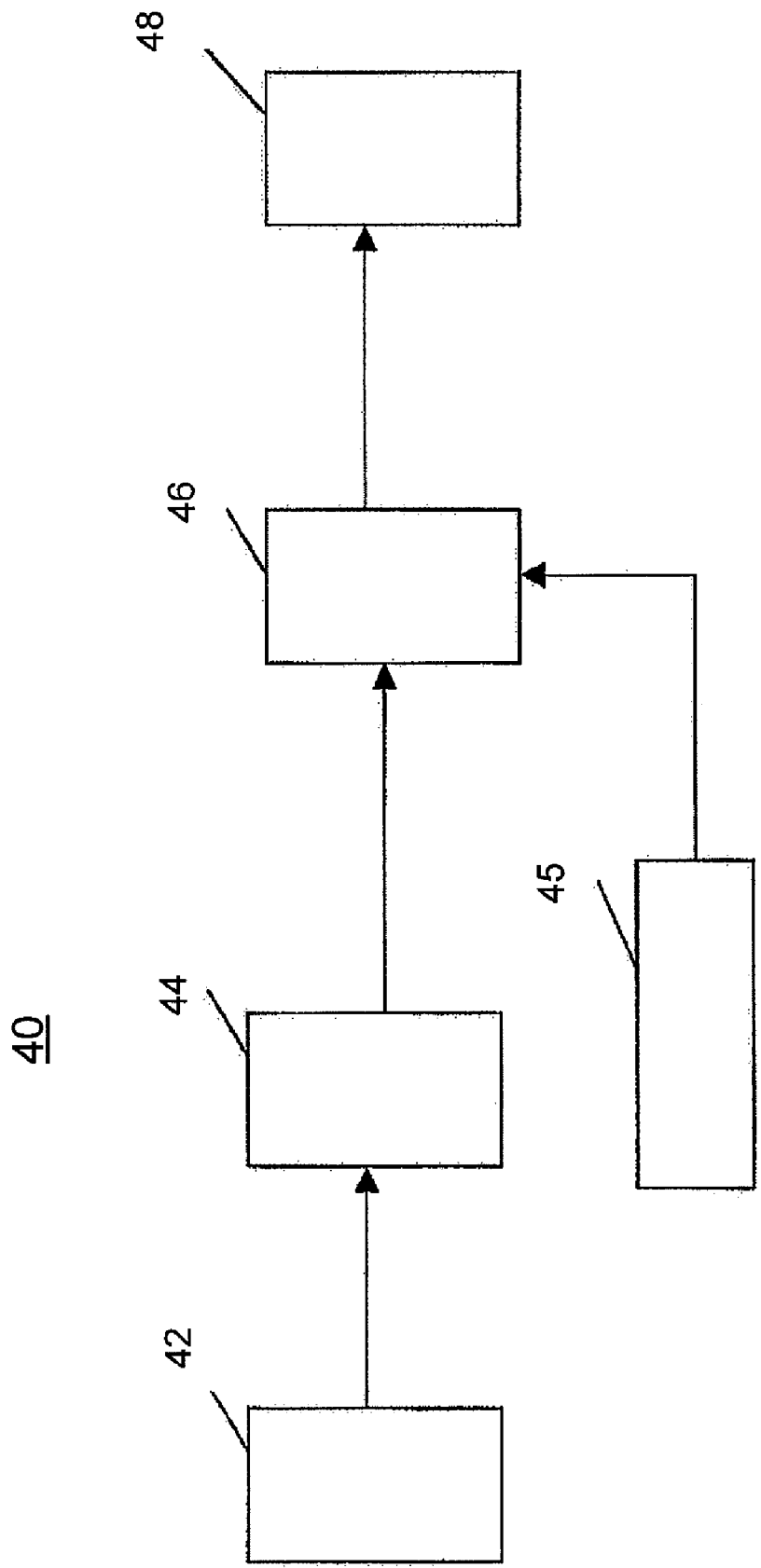
FIG. 5 presents in a schematic way an embodiment of the method according to the invention.

FIG. 5 presents in a schematic way an embodiment of the method according to the invention. In according to the technical measure of the invention the method 40 is provided wherein pre-determined constraints, notably joint constraints, are provided at step 42 and a model comprising parameters describing individual parameters of the object portions is selected. Additionally, orientation from one or more OMU's is provided as input at step 42.

At step 44 an a-priori estimate of the considered distance between the two points A and B is written as a function of unknown/uncertain body proportions, OMU to segment orientation and possibly other modeling parameters used in 42. This is accomplished by identifying a kinematic chain and using the model relations from step 42, as set forth with reference to FIG. 3. Additionally the correlations between the different model parameters may be computed.

At step 46 an update is performed using output data from the step 44 and additional input data 45, comprising information about a known or constant distance between two points A and B. The known or constant distance on the object can be obtained in accordance with the procedure of the foregoing. Model parameters such as the (relative) dimensions of the object portions and the orientation of the OMU with respect to the joints are determined or updated to comply with the additional input data, preferably in a statistical sense.

One possible procedure to perform the calibration is as follows. First, a step 42 suitable pre-determined constraints and orientation data. These can include on regression equations, a scaling model or previous calibration movements.

Subsequently at step 44 an a priori estimate of the parameters to be estimated and their covariance is made. These parameters are at least the (relative) dimensions of the object portions and the orientation of one or more OMU's with respect to a joint. In the linear case, if the parameters are contained in the array x, the correlation of these parameters is expressed as $Qx = E(x \cdot x^T)$. By identifying a kinematic chain, the a priori distance $\hat{D}(x)$ is computed given the predetermined constraints and the orientation measured by OMU's.

At step 46 the a-priori estimated distance or distance change is compared to the additional input data from step 45. Using this comparison and the correlation (covariance) between the parameters x an improved estimate of the parameters is computed. The model parameters are adjusted to have the model estimate correspond to the actual distance that is known by measuring or instruction to the user. A complementary per se known Kalman routine may be used. The uncertainty of the measurement and the correlation between the parameters Qx is taken into account.

In 48 the estimated or improved parameters, notably relative body portions and the orientation of the OMU with respect to the joints, are stored.

Many different distances within the body could be used for the calibration. Three different ways proposed to perform this calibration are:

A. Asking the user to keep one point of the body in contact or fixed distance with another point, see for example FIG. 4.

B. The subject makes a movement in which he/she is asked to keep some distance constant, for example by holding a stick by two hands and displacing hands. Alternatively, the person may stand on a horizontal surface, preferably with some different poses of the lower extremities, as is schematically shown in FIG. 2. In this case the distance in the vertical direction is known, assuming flat surface. The person is allowed to move during measurement, as long as the chain is not broken. This is beneficial to quickly obtain a large number of different relations so that the parameters can be further refined.

Due to the fact that all relations are preferably expressed in statistical terms the reliability of the different sensor components must be set. This has the advantage that the calibration can also be performed in environments in which the (earth) magnetic field is disturbed. In this case the reliability of the magnetometer must be set to a corresponding low value.

Except an improved estimate of calibration parameters, the same method can be used to improve the segment kinematics directly and in-use.

The calibration results will strongly improve if the person is assuming multiple poses while holding the segments in contact. Furthermore touching multiple points on the body will also strongly improve calibration. This makes for a quick and accurate calibration method that can be used without specialized additional equipment or persons.

Separate from a known distance or a constant distance, also a priori assumptions about the accelerations can be used. When the person to be recorded is known to accelerate forwards, the yaw of the OMU's with respect to each other can be determined without the use of magnetometers.

The calibration parameters are generally linked via an underlying model and are therefore correlated. Because the correlation between the different parameters is known, also parameters that are not directly measured can be adjusted. E.g. the leg length can be adjusted once the arm length is measured because it is known in a statistical sense how the leg length is correlated with the arm length.

Figure 6:
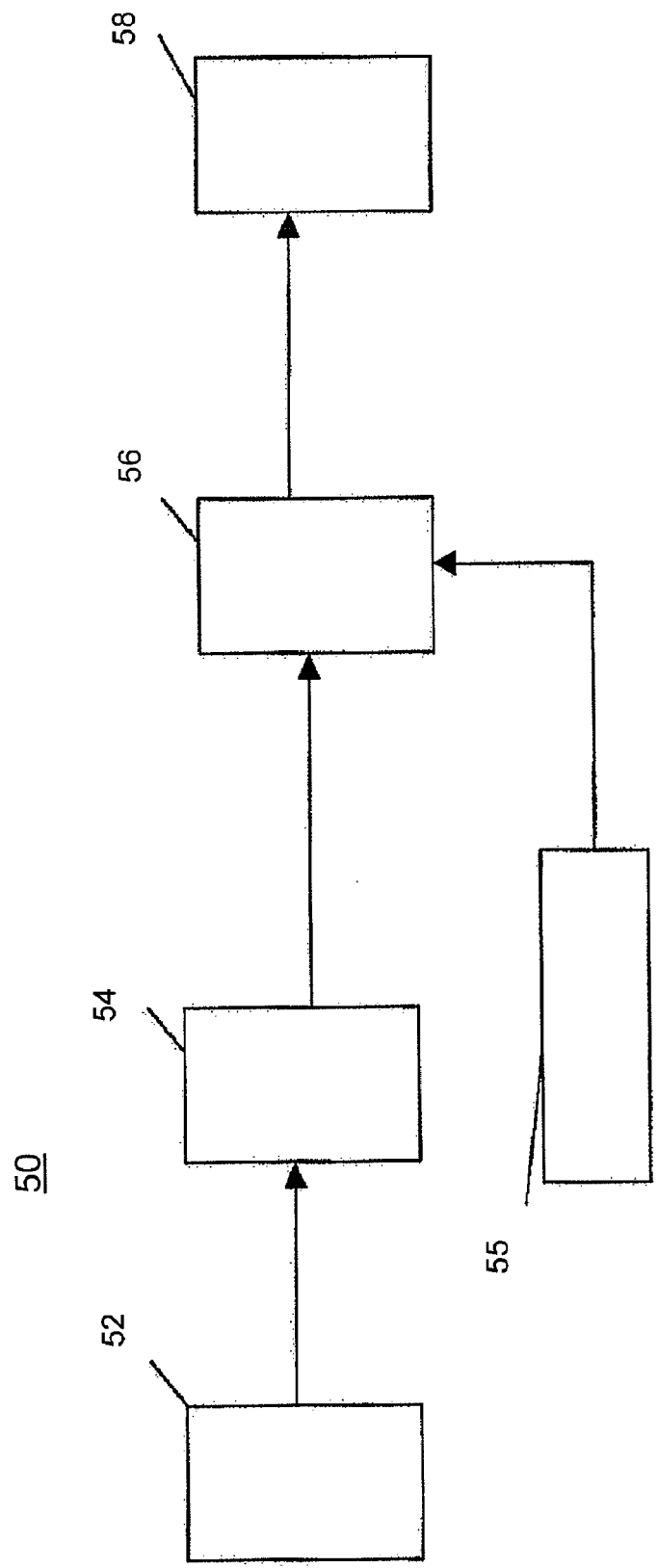
FIG. 6 presents in a schematic way a further embodiment of the method according to the invention.

FIG. 6 presents in a schematic way a further embodiment of the method according to the invention. The method is not confined to situations in which some distance is known or known to be constant, but requires an acceleration to be measured on some point on at least two body portions, in addition to the orientation. This makes the procedure applicable for in-use calibration. The subject may perform calibration by making an arbitrary movement such as the movements he/she wishes to record. The system will then perform in-use calibration of the orientation of the OMU with respect to the joints, as well as joint position with respect to the OMU.

The method that must be used with in-use calibration is different from calibration as described with reference to FIG. 4 in that at step 55 not the information about a known fixed or constant distance is used, but the acceleration as measured using an OMU. The acceleration can be obtained from the accelerometers in the OMU. Advantage is that these acceleration measurements are readily available and a separate calibration is not required and no magnetometers are required. Thus, in the present embodiment of the method according to the invention at step 52 predetermined constraints, notably joint constraints, and measurement data from orientation measurement units, namely OMU's, is obtained.

At step 54 the predetermined constraints are used to formulate the a priori estimated acceleration of two points on respective body portions as a function of parameters to be estimated, notably position and orientation of the OMU with respect to the joints.

Preferably suitable correlation between parameters is obtained. At step 56 a suitable update of parameters is being performed based on acceleration data provided at step 55. Finally, the improved parameters are provided and stored at step 58.

The operation of the present embodiment of the method according to the invention will be explained with reference to two object portions (segments) connected by a joint. Two segments are assumed to be connected by a joint which characterized by some average centre of rotation. The position of the orientation measurement unit, notably an OMU with respect to the joint is given by vectors $r_A$ and $r_B$ for the two OMU's 302 and 304 in FIG. 3, respectively. The movement of the OMU 302 and 304 is related. This relation is a function of the distances $r_A$ and $r_B$, the measured OMU kinematics and the orientation of the OMU. Given a sufficient number of recorded movements these quantities ($r_A$ and $r_B$) can be estimated. This does not only yield information about the position of the OMU with respect to the joints but also the orientation of the OMU with respect to the joints.

The method described here is a powerful method because it relieves the subject from performing specialized calibration movements. Because it does not have to assume a movement is performed correctly, it is less error prone. The accuracy may preferably be computed and may be fed back to the user.

The method need not only be performed over two adjacent segments, but can be generalized to multiple segments that are connected. It is further noted that by combining multiple of the above described sequences a yet improved calibration can be obtained. The calibration preferably is performed in an iterative process. Because of local disturbances of the earth magnetic field, the orientation may not be accurate in all directions. This specific uncertainty can be taken into account. Instead of comparing an acceleration or angular velocity directly, also a derived quantity might be used such as the mathematically integrated acceleration (velocity) or position.

Other antropometric or biomechanical relations that can be taken into account to identify the human motion system in even more detail are an a priori knowledge about the spine and shoulder rhythm; suitable neurological constraints imposed by e.g. reflex loops; suitable power constraints originating from the limited power a user can generate while in a certain pose.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

The invention claimed is:

1. A motion tracking system for tracking a movement of an object in a three-dimensional space, the object being composed of object portions having individual dimensions and mutual proportions and being sequentially interconnected by joints, the system comprising:

orientation measurement units for measuring data related to at least an orientation of the object portions, wherein the orientation measurement units are arranged in positional and orientational relationships with respective object portions and having at least orientational parameters;

a processor for receiving data from the orientation measurement units, the processor comprising a module for deriving orientation and/or position information of the object portions using the received data, characterized in that the processor further comprises a calibration unit arranged to calculate calibration values for determining at least mutual proportions of the object portions and at least orientational parameters of the orientation measurement units based on received data, predetermined constraints and additional input data comprising knowledge about a distance between at least two points and/or knowledge about an acceleration of at least two object portions connected by a joint.

2. A motion tracking system according to claim 1, wherein the pre-determined constraints comprise geometrical and/or mechanical constraints pertaining to the sequential interconnection of the object portions.

3. A system according to claim 1, wherein the predetermined constraints are statistically expressed.

4. A system according to claim 1, the measurement data further relating to the position and/or orientation of the orientation measurement unit, wherein the calibration unit is further arranged to statistically express the parameters of the orientation measurement units.

5. A system according to claim 3, wherein the calibration unit is further arranged to calculate a statistical error assignable to an individual parameter conceived to be determined.

6. A system according to claim 5, wherein the calibration unit is further arranged to assign a weighting factor to an individual dimension and/or mutual proportion in relation with the calculated statistical error.

7. A system according to claim 6, further comprising a control unit arranged to control the processor for discarding measurement data from an orientation measurement unit which provides data used for calculation of a parameter with a reduced weighting factor.

8. A system according to claim 1, wherein the calibration unit is arranged to use a pre-defined model of the object for determining dimension and/or mutual proportion of the object portions and/or orientational parameters of the orientation measurement units.

9. A system according to claim 8, wherein the calibration unit is further arranged to use an estimate of parameters of the orientation measurement units.

10. A system according to claim 8, wherein the individual dimensions and/or mutual proportions of the object portions are a-priori correlated.

11. A system according to claim 1, wherein the orientation measuring device comprises an inertial sensing unit.

12. A system according to claim 11, wherein the orientation measurement unit is further assigned with positional parameters, the measurement data comprising acceleration data, measured at least with respect to two points definable of the respective body portions connected by at least one joint, the calibration unit being further arranged to calculate calibration values for determining individual dimensions of the object portions and positional parameters of the orientation measurement units based on received data, pre-determined constraints and additional input data.

13. A system, according to claim 1, wherein the calibration unit is arranged to operate iteratively.

14. A method for tracking a movement of an object being composed of object portions having individual dimensions and mutual proportions and being sequentially interconnected by joints in a three-dimensional space, comprising:

measuring data related to at least an orientation of the object portions with orientation measurement units, wherein the orientation measurement units are arranged in positional and orientational relationships with respective object portions having at least orientational parameters;

receiving data from the orientation measurement units;

deriving orientation and/or position information of the object portions using the received data;

calculating calibration values for determining at least mutual proportions of the object portions and at least orientational parameters of the orientation measurement units based on received data, predetermined constraints and additional input data comprising knowledge about a distance between at least two points and/or knowledge about an acceleration of at least two object portions connected by a joint.

15. A method according to claim 14, wherein for the predetermined constraint knowledge about geometrical and/or mechanical constraints pertaining to the sequential interconnection of the object portions is selected.

16. A method according to claim 14, wherein the predetermined constraints are statistically expressed.

17. A method according to claim 14, the measurement data further relating to the position and/or orientation of the orientation measurement unit, wherein the parameters of the orientation measurement units are statistically expressed.

18. A method according to claim 16, wherein a statistical error assignable to an individual dimension and/or mutual proportion is calculated.

19. A method according to claim 18, wherein a weighting factor for the individual dimension and/or mutual proportion is assigned in relation with the calculated statistical error.

20. A method according to claim 19, wherein measurement data leading to a calculation of a parameter with a reduced weighting factor is discarded.

21. A method according to claim 14, wherein a predefined model of the object is used for determining individual dimensions and/or mutual proportions of the object portions and/or parameters of the orientation measurement units.

22. A method according to claim 21, wherein an estimate of parameters of the orientation measurement units is used.

23. A method according to claim 21, wherein the individual parameters of the object portions are a-priori correlated.

24. A method according to claim 14, wherein the measuring data are obtained using an orientation measuring device comprises, preferably an inertial measurement unit.

25. A method according to claim 24, wherein the orientation measurement unit is further assigned with positional parameters, the measurement data comprising acceleration data measured at least with respect to two points defined on respective body portions connected by at least one joint, the calibration unit calculating calibration values for determining individual dimensions of the object portions and positional parameters of the orientation measurement units based on received data and predetermined constraints.

26. A method, according to claim 14, wherein the method steps are carried out iteratively.

27. A medical rehabilitation system comprising the motion tracking system according to claim 1.

28. An animation system comprising the motion tracking system according to claim 1.

29. A gaming system comprising a computer and the motion tracking system according to claim 1.

* * * * *